United States Patent
Rothschild et al.

(10) Patent No.: US 7,555,099 B2
(45) Date of Patent: Jun. 30, 2009

(54) X-RAY INSPECTION WITH CONTEMPORANEOUS AND PROXIMAL TRANSMISSION AND BACKSCATTER IMAGING

(75) Inventors: Peter J. Rothschild, Boston, MA (US); Jeffrey R. Schubert, Somerville, MA (US); Aaron D. Pailes, Acton, MA (US)

(73) Assignee: American Science and Engineering, Inc., Billerica, MA (US)

( * ) Notice: Subject to any disclaimer, the term of this patent is extended or adjusted under 35 U.S.C. 154(b) by 78 days.

(21) Appl. No.: 11/834,888

(22) Filed: Aug. 7, 2007

(65) Prior Publication Data
US 2008/0037707 A1    Feb. 14, 2008

Related U.S. Application Data

(60) Provisional application No. 60/822,162, filed on Aug. 11, 2006.

(51) Int. Cl.
*G01N 23/20* (2006.01)
(52) U.S. Cl. .......................................... 378/90; 378/57
(58) Field of Classification Search ................. 378/57, 378/86, 87, 88, 89, 90
See application file for complete search history.

(56) References Cited

U.S. PATENT DOCUMENTS

| | | |
|---|---|---|
| 3,961,186 A | 6/1976 | Leunbach |
| 4,047,029 A | 9/1977 | Allport |
| 4,380,817 A | 4/1983 | Harding et al. |
| 4,525,854 A | 6/1985 | Molbert et al. |
| 4,768,214 A | 8/1988 | Bjorkholm |
| 4,799,247 A | 1/1989 | Annis et al. |
| 4,864,142 A | 9/1989 | Gomberg |
| 4,884,289 A | 11/1989 | Glockmann et al. |
| 5,016,173 A * | 5/1991 | Kenet et al. ................. 382/128 |
| 5,065,418 A | 11/1991 | Bermbach et al. |
| 5,253,283 A | 10/1993 | Annis et al. |
| 5,313,511 A | 5/1994 | Annis et al. |
| 5,428,657 A | 6/1995 | Papanicoloploulos et al. |
| 5,430,787 A | 7/1995 | Norton |
| 5,600,303 A | 2/1997 | Husseiny et al. |
| 5,600,700 A | 2/1997 | Krug et al. |
| 5,638,420 A | 6/1997 | Armistead |
| 5,642,393 A | 6/1997 | Krug et al. |

(Continued)

FOREIGN PATENT DOCUMENTS

EP        0 864 884 A2    4/1998

(Continued)

OTHER PUBLICATIONS

Jul. 8, 2007, International Search Report.

(Continued)

*Primary Examiner*—Chih-Cheng G Kao
(74) *Attorney, Agent, or Firm*—Bromberg & Sunstein LLP

(57) ABSTRACT

An X-ray imaging inspection system for bags and packages. Transmission imaging is performed using a fan beam and a segmented detector, while scatter imaging is performed with a scanned pencil beam, with both beams active simultaneously. Cross-talk between the beams is mitigated by a combination of shielding, scatter detector design, positioning and orientation, and image processing. Image processing subtracts the measured radiation scattered from the transmission beam into the scatter detectors, reducing cross-talk.

16 Claims, 3 Drawing Sheets

U.S. PATENT DOCUMENTS

| | | | |
|---|---|---|---|
| 5,692,029 | A | 11/1997 | Husseiny et al. |
| 5,763,886 | A | 6/1998 | Schulte |
| 5,764,683 | A | 6/1998 | Swift et al. |
| 5,910,973 | A | 6/1999 | Grodzins |
| 5,917,880 | A | 6/1999 | Bjorkholm |
| 5,940,468 | A | 8/1999 | Huang et al. |
| 5,954,650 | A * | 9/1999 | Saito et al. .................. 382/128 |
| 5,974,111 | A | 10/1999 | Krug et al. |
| 6,151,381 | A | 11/2000 | Grodzins et al. |
| 6,192,104 | B1 | 2/2001 | Adams et al. |
| 6,249,567 | B1 | 6/2001 | Rotschild et al. |
| 6,282,260 | B1 | 8/2001 | Grodzins |
| 6,320,933 | B1 | 11/2001 | Grodzins et al. |
| 6,421,420 | B1 | 7/2002 | Grodzins |
| 6,459,764 | B1 | 10/2002 | Chalmers et al. |
| 6,546,072 | B1 | 4/2003 | Chalmers |
| 6,661,867 | B2 | 12/2003 | Mario |
| 6,687,326 | B1 | 2/2004 | Bechwati et al. |
| 7,072,440 | B2 | 7/2006 | Mario |
| 7,092,485 | B2 | 8/2006 | Kravis |
| 2005/0185757 | A1 | 8/2005 | Kresse et al. |
| 2005/0259781 | A1 * | 11/2005 | Ying et al. ..................... 378/5 |

FOREIGN PATENT DOCUMENTS

| | | |
|---|---|---|
| GB | 2 277 013 | 2/1994 |
| WO | WO 98/20366 | 7/1997 |
| WO | WO 2004/043740 | 5/2004 |

OTHER PUBLICATIONS

Amer. Sci & Engineering, May 17, 2006, Press release for Gemini System.

* cited by examiner

X-RAY INSPECTION WITH CONTEMPORANEOUS AND PROXIMAL TRANSMISSION AND BACKSCATTER IMAGING

This application claims priority from U.S. provisional patent application Ser. No. 60/822,162, Aug. 11, 2006, entitled "X-Ray Inspection with Contemporaneous and Proximal Transmission and Backscatter Imaging," which is incorporated herein by reference.

TECHNICAL FIELD

The present invention relates to methods and systems for inspecting objects by means of penetrating radiation, and more particularly, to inspection of objects by substantially contemporaneous transmission and scatter probes.

BACKGROUND OF THE INVENTION

Standard x-ray transmission imaging systems have been used for security, medical, and inspection applications for many decades. Typically, medical transmission x-ray images have been obtained using cone beams of x-rays and utilizing x-ray film as the detection medium. More recently, fan beams of x-rays have been used in conjunction with linear segmented detector arrays to create two dimensional images of objects which are conveyed through the fan beam, between the x-ray source and the detector array. This is also the standard approach for examining small bags or packages for security applications, such as at airports. The transmission image obtained may be a single-energy image, using a single end-point energy x-ray tube and a detector array where each array element consists of only one detector channel.

Images based on differential transmission or scatter as a function of the energy of incident radiation may be obtained using an x-ray source that alternates between two end-point energies, or, alternatively, by employing a dual-energy segmented detector array. Such arrays have two detector channels per array element. One detector channel is sensitive to the lower energy x-rays, while the second channel (which often also contains an x-ray filter) preferentially detects the higher energy x-rays. By taking the ratio of the two signals from the low and high energy channels, dual-energy transmission images can be obtained, which allow the average effective atomic number Z of materials at each location in the image to be determined. This allows materials to be crudely separated into either low-Z (organic), intermediate-Z, or high-Z (metallic) materials. This information can then be overlaid on the black and white transmission image, typically using a color palette, to create a color image which conveys the material identification information to the operator.

Backscatter x-ray imaging has been used in the last couple of decades to provide a means of more reliably detecting and imaging organic materials that have been concealed in bags and packages, and even large cargo containers and vehicles. Instead of using a fan beam of x-rays, these systems typically use a scanning pencil beam of x-rays, also know as a "flying spot". Backscatter images are created by measuring the amount of x-ray energy that is Compton scattered out of the beam as each part of the object is sequentially illuminated by the beam. The Compton scattered x-rays are typically detected in large-area detectors which have been optimized for detecting the relatively low energy scattered x-rays. By raster scanning the pencil beam across the object being scanned while conveying the object though the scanning beam, a complete two-dimensional backscatter image of the object is obtained. Since the Compton scatter at lower x-ray energies (below about 250 keV) tends to be most sensitive to the organic regions of the object, the method can be used to highlight these regions.

The combination of x-ray transmission and backscatter techniques has previously been taught, for example, in U.S. Pat. No. 6,151,381 ("Gated Transmission and Scatter Detection," wherein separate and temporally gated sources are used for transmission and backscatter imaging) and U.S. Pat. No. 6,546,072 ("Transmission-Enhanced Scatter Imaging," wherein the same source is used for both transmission and backscatter images). Both of the foregoing patents are incorporated herein by reference. Systems using both transmission and backscatter imaging have either required identical source spectra for the two modalities (in cases where a single source is used for both) or else have had to contend with cross-talk issues, due especially to the scattered photons from the typically higher-energy or higher-flux transmission fan beam impinging on the scatter detectors.

SUMMARY OF THE INVENTION

In accordance with preferred embodiments of the present invention, methods and a system are provided for inspecting an object. The system has two sources of penetrating radiation, the first emitting a fan beam and the second emitting a scanned beam of penetrating radiation. The system has a segmented array of detector elements for measuring the intensity of penetrating radiation from the fan beam transmitted through the object as well as at least one scatter detector for detecting penetrating radiation scattered out of the scanning pencil beam by the object. Finally, the system has a processor for forming at least one image depicting transmission and scatter features which can be displayed to an operator.

In further embodiments, the segmented detector array may be a dual-energy detector array, and the backscatter detectors may be collimated so that they preferentially detect x-rays scattered out of the scanning beam. An attenuating barrier may be disposed between the transmission imaging subsystem and the scatter imaging subsystem in such a manner as to reduce cross talk.

The system may provide for adjustment of the aspect ratio and size of the transmission and scatter images with software algorithms so that the size and shape of the inspected object looks similar in both images. The contribution in the scatter image due to cross talk may be subtracted, either in hardware or software, from the scatter image. In some embodiments, the scatter detector signal is measured when the scanning pencil beam is not illuminating the object to determine the contribution due to cross talk and this measured signal is subtracted from the scatter detector signal when the scanning pencil beam illuminates the object.

In accordance with yet further embodiments of the invention, one or more scatter detectors may preferentially detect scattered x-rays in one energy range and one or more scatter detectors may preferentially detect x-rays in another energy range. Signals from the two sets of detectors may then be combined to extract additional information regarding the effective atomic number of the imaged object.

BRIEF DESCRIPTION OF THE DRAWINGS

The foregoing features of the invention will be more readily understood by reference to the following detailed description taken with the accompanying drawings.

DETAILED DESCRIPTION OF EMBODIMENTS OF THE INVENTION

Figure 1:
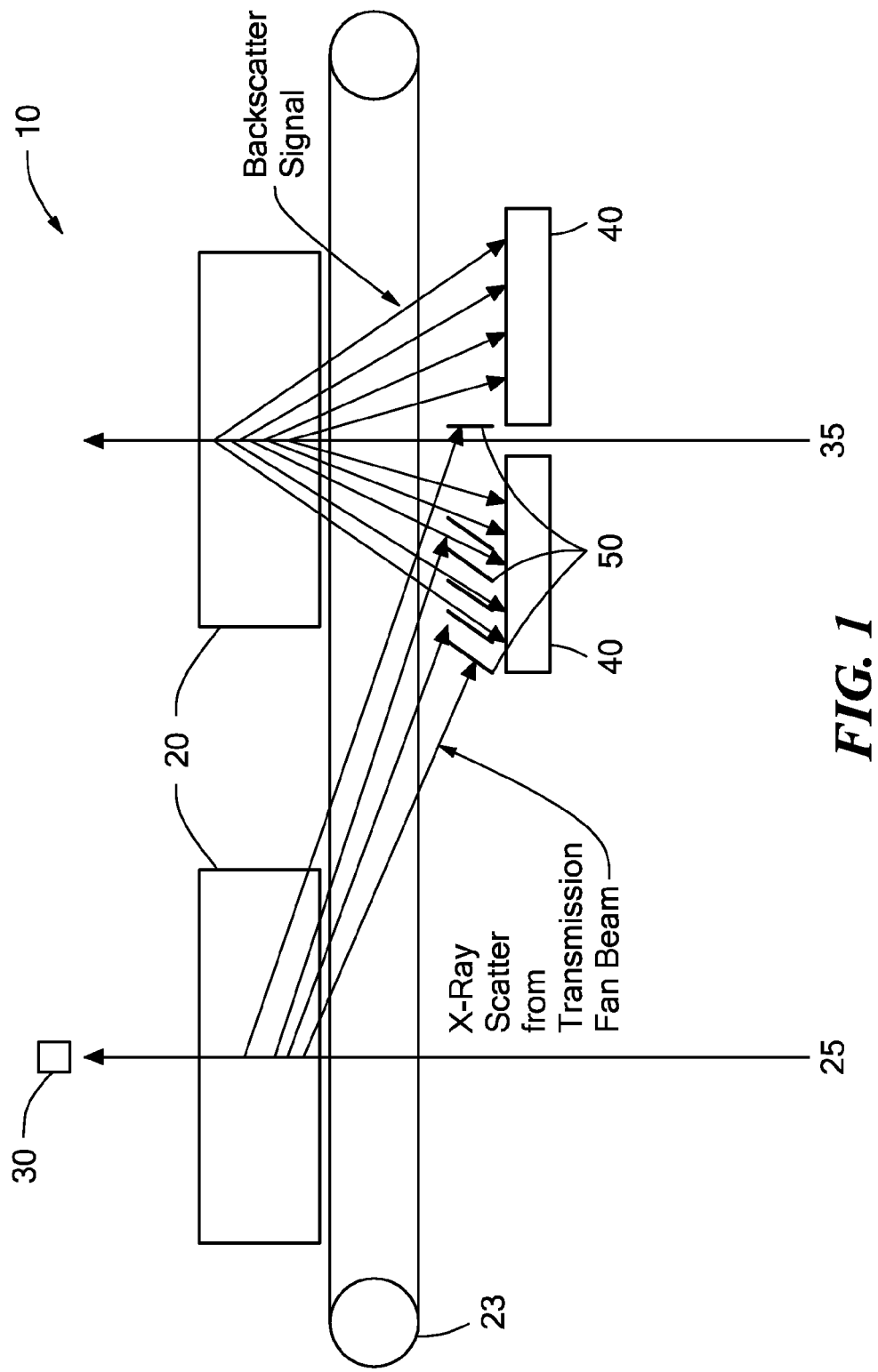
FIG. 1 is a schematic illustration of a transmission and scatter imaging inspection system with detector collimating vanes, in accordance with embodiments of the present invention.

Embodiments of the present invention provide methods and systems for overcoming issues of cross-talk between transmission and scatter imaging modalities. These methods and systems also provide for processing the images in software such that the aspect ratio of the transmission and backscatter images that are presented to an operator are comparable, even though the imaging is performed by different sources, with the object under inspection at different positions.

Embodiments of the invention are described herein in terms of x-ray radiation, however, it is to be understood that the teachings and scope of the claimed invention extends to penetrating radiation of any kind, including gamma rays, etc.

By combining an x-ray transmission imaging system that uses a fan beam and a segmented detector array, with a scatter imaging system that uses a scanning pencil beam, a powerful imaging system is obtained that incorporates the best of both technologies. The transmission image is a high-resolution image, where the image resolution is determined by the size of the individual detector array elements. By using a dual-energy x-ray source, or a dual-energy detector array, the transmission image can also display the effective atomic number Z of the objects being imaged. The resolution of the backscatter image is determined by the width of the pencil beam that is used to scan the object: the narrower the beam, the higher the resolution. However, as the width of the beam is reduced, the number of x-rays in the beam is also reduced, decreasing the available photon statistics and increasing the apparent graininess of the backscatter image. The size of the beam that is used is therefore a tradeoff between image quality and resolution.

A compact imaging system 10 that incorporates separate transmission and backscatter imaging subsystems is described with reference to FIG. 1. An object 20 being inspected, such as a package or bag, is first conveyed on a conveyor 23 through an x-ray fan beam 25, and the transmission image is formed by measuring the x-ray intensity that is transmitted through the object to each of the detector elements in a segmented transmission detector array 30. As the object 20 is conveyed further through the inspection tunnel of the system, it passes through the plane of the raster-scanning pencil beam 35 of a backscatter imaging system. The backscatter image is formed by measuring the intensity of the Compton scattered radiation that is detected by scatter detectors 40 placed under the conveyor 23, or on the walls or roof of the inspection tunnel.

Cross-Talk Reduction between Imaging Subsystems

A major technical challenge to the incorporation of transmission and scatter modalities into one compact imaging system is reducing the leakage of x-ray radiation between the two imaging systems. For practical reasons of throughput and cost, it is preferable that both the transmission x-ray fan beam and the backscatter x-ray pencil beam be energized simultaneously. This means that x-rays scattered out of the transmission fan beam 25 by the object 20 (or off any surfaces of the inspection system itself) will be detected in the backscatter detectors 40. Similarly, x-rays scattered out of the pencil beam 35 by the object 20 will also be detected in the transmission detector array 30. Because the backscatter detectors are large relative to the transmission detector elements, and because the transmission subsystem uses a fan beam rather than a pencil beam, the cross-talk (or leakage) problem is almost exclusively one-way: that is, radiation is scattered out of the transmission fan beam into the backscatter detectors. This cross-talk manifests itself as brighter, cloudy regions in the backscatter image, or in its more extreme manifestation, as vertical banding in the backscatter image.

We have found that features incorporated into the system hardware can reduce the effects of x-ray "cross-talk," such as collimation vanes, careful design and placement of the backscatter detectors, and X-ray attenuating barriers between the transmission imaging subsystem and the backscatter imaging subsystem.

Examples of collimation vanes 50 are shown in FIG. 1. The vanes are designed so that the field of view ("FOV") of the backscatter detectors is limited to detecting backscatter that originates from the plane that contains the pencil beam of the backscatter imaging subsystem. X-rays which are scattered out of the fan beam of the transmission imaging subsystem are not able to pass through the collimators, and therefore do not contribute in a negative way to the backscatter signal. A problem with angled collimator vanes placed on the right hand, backscatter detector 40 shown in FIG. 1, is that such vanes would also reduce the real backscatter signal coming from the scanning pencil beam 35. Thus, a single collimator vane, parallel to the pencil beam 35, is used for the right backscatter detector. However, X-rays scattered from the transmission fan beam can still enter this detector, degrading the quality of the backscatter image.

Figure 2:
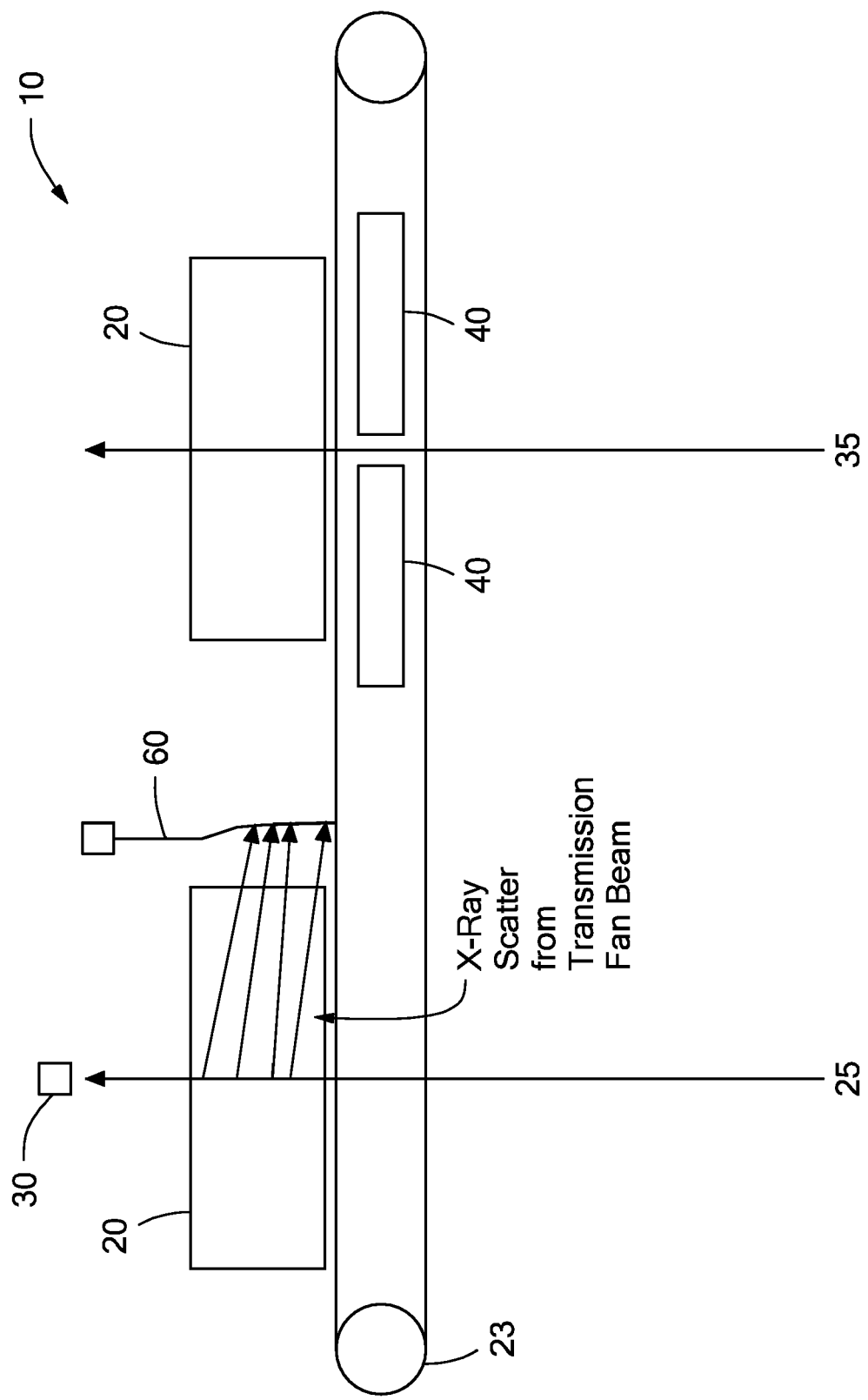
FIG. 2 depicts the interposition of an x-ray attenuating flexible barrier in a transmission and scatter imaging inspection system in accordance with embodiments of the present invention.

To further reduce unwanted "cross-talk" between X-ray beams, a second method of reducing the unwanted cross-talk between the transmission and backscatter imaging subsystems is to place an x-ray attenuating flexible barrier, such as a lead curtain 60, between the two subsystems, as depicted, for example, in FIG. 2. The barrier (or barriers) could also consist of swinging doors, which are spring-loaded to return them to the closed position. In this embodiment, the x-rays scattered out of the transmission fan beam are blocked by the attenuating barrier before they can enter the backscatter detectors. It is preferred that the length of the curtain (or other barrier) should be such that it cannot be pushed or pulled by the object 20 into the plane that contains either the fan beam or the pencil beam. We have found that such a screen reduces the effect of transmission beam X-rays scattered into the backscatter detectors.

Cross-talk Subtraction

In addition to hardware methods to reduce x-ray cross-talk, such as those described above, the induced signal in the backscatter detectors due to residual cross-talk from the transmission imaging system can be subtracted to remove it from the backscatter signal. This is accomplished by measuring the signal from the backscatter detectors when the backscatter pencil beam is momentarily off. For example, the scanning pencil beam can be created using a rotating chopper wheel, which contains a number of apertures. As each aperture is illuminated by the x-ray tube, an x-ray pencil beam emerges from the aperture, sweeping across the inspection tunnel as the chopper wheel rotates. During the brief time interval when one aperture has just left the illuminated region and just before the next aperture has entered the illuminated region, the pencil beam is essentially off During this brief "beam-off" time interval, the signal from the backscatter detectors is due mainly to the cross-talk from the transmission fan beam, which is always energized. This signal is used to measure the instantaneous intensity of the transmission fan beam flux scattered into the scatter detectors for that scan line, which can then be subtracted from that scan line in the backscatter image to remove the cross talk signal. This subtraction can be done either in the data acquisition electronics, or later in processing before the image is displayed to the operator. The subtraction can be performed using a processor with an associated memory containing instructions that the processor executes to perform operations including the aforementioned subtraction. As used herein, and in any appended claims, the term "memory" shall include, without limitation, a solid state memory, a magnetic medium, such as a hard disk, or any other device containing instructions that can be executed by the processor.

Figure 3:
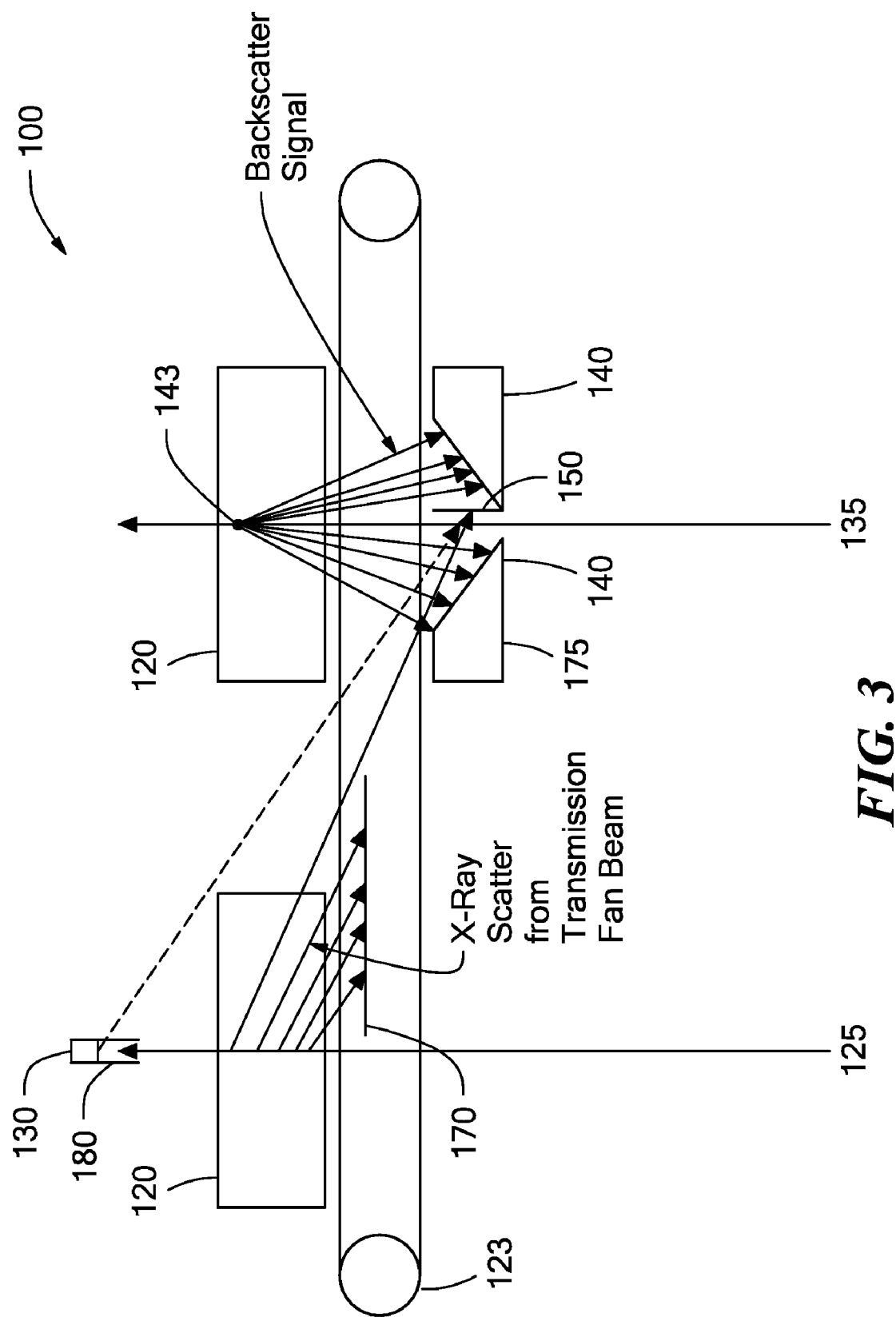
FIG. 3 is a schematic illustration of another embodiment of a transmission and scatter imaging inspection system with collimating vanes and detector screening.

In other embodiments of the invention, cross talk between the transmission imaging subsystem and the backscatter imaging subsystems is mitigated by combinations of collimation vanes, shields and preferred scatter detector orientations, as shown in the system 100 in FIG. 3. An object 120 being inspected, such as a package or bag, is first conveyed on a conveyor 123 through an X-ray fan beam 125. Note the following improvements over the system of FIG. 1:

(a). The active surface of the backscatter detectors 140 can be angled towards the point 143 from which the backscatter signal emanates. This geometry maximizes the detection of the backscatter signal from the backscatter beam 135, while minimizing the detection of cross talk from the transmission beam. This geometry also eliminates the need for collimator vanes on the left hand detector. All other surfaces 175 of the backscatter detectors may be lined with a shielding material, such as lead, to minimize stray X-ray detection.

(b) A single vertical vane 150 protects the active face of the right hand backscatter detector from detecting scattered radiation from the transmission beam 125.

(c) A lead shield 170 under the conveyer belt 123 near the transmission beam shields the left hand backscatter detector 140 from detecting scattered radiation from the transmission beam.

(d) collimators 180 in front of the transmission detectors prevent radiation scattered out of the transmission beam off the front face of the transmission detectors 130 from reaching the backscatter detectors 140.

Aspect Ratio Correction

Because the transmission image and the backscatter image are acquired through two different methods, the images, in general, will have a different aspect ratio. The same object, therefore, can appear to have a very different shape and size in each of the two images. In order to make this less confusing to the operator, the current invention includes a software method for adjusting the aspect ratio of either (or both) the transmission or backscatter images, so that they appear to have the same size and shape when displayed to the operator. Typically, the width of the object (along the direction of conveyance) will be similar in both the transmission and backscatter images. The height of the object (perpendicular to the direction of conveyance) will often be different in the two images, however. In order to correct for this, a known scaling factor can be applied to one of the images to ensure the height of the object is the same in each image. Alternatively, a software algorithm can be employed which determines the height of the object in each image, and the images can be scaled accordingly.

All of the heretofore described embodiments of the invention are intended to be merely exemplary and numerous variations and modifications will be apparent to those skilled in the art. For example, while backscatter imaging is described above, in other embodiments of the invention, other types of scatter imaging may be employed. Another example would be a system containing only one X-Ray source, in which both the transmission fan beam and the scanning pencil beam are extracted from the same source. All such variations and modifications are intended to be within the scope of the present invention as defined in any appended claims.

What is claimed is:

1. A system for inspecting an object, the system comprising:
   a. a first radiation source that emits a fan beam of penetrating radiation;
   b. a segmented array of detector elements for measuring the intensity of penetrating radiation transmitted through the object by the first radiation source;
   c. a second radiation source that emits a scanning pencil beam of penetrating radiation;
   d. at least one scatter detector for detecting penetrating radiation scattered out of the scanning pencil beam by the object; and
   e. a processor, a memory, and a display, the memory containing instructions that cause the processor:
   to subtract a background signal from a measured signal from the scatter detector, the background signal measured by the scatter detector when the scanning pencil beam is not illuminating the object, thereby forming a corrected measured scatter signal, and
   to display on the display the corrected measured scatter signal and a measured transmission signal from the segmented array of detector elements for use in inspecting the object.

2. A system according to claim 1, wherein the first radiation source emitting the fan beam and the second radiation source emitting the scanning pencil beam are the same radiation source.

3. A system according to claim 1, wherein the at least one scatter detector includes means for collimating penetrating radiation such that penetrating radiation from the scanning pencil beam is preferentially detected.

4. A system according to claim 1, wherein the at least one scatter detector includes a substantially planar face, the planar face sensitive to incident radiation, the planar face characterized by a normal to the face and wherein the normal to the face is oriented substantially towards a point of incidence of the scanning pencil beam with the object.

5. A system according to claim 4, wherein at least one surface of the scatter detector other than the planar face is shielded to reduce detection of penetrating radiation from the fan beam.

6. A system according to claim 1, further including a barrier disposed between the fan beam and the at least one scatter detector such that a measured signal from the scatter detector due to the fan beam is reduced.

7. A system according to claim 6, wherein the barrier is a curtain disposed substantially parallel to the fan beam.

8. A system according to claim 6, wherein the barrier is a swinging shield disposed substantially parallel to the fan beam.

9. A system according to claim 6, wherein the barrier is a shield disposed substantially perpendicular to the fan beam.

10. A system according to claim 1, wherein the memory further includes instructions to cause the processor to adjust the aspect ratio and size of the measured transmission signal and the corrected measured scatter signal such that the size and shape of the object appear similar in a display of the measured transmission signal and in a display of the corrected measured scatter signal.

11. The system according to claim 1, wherein the segmented array of detector elements includes a first set of elements that measure radiation in a first energy range and a second set of elements that measure radiation in a second energy range.

12. A system according to claim 11, wherein the memory further includes instructions to cause the processor to determine the effective atomic number of at least one portion of the object using measurements from the first set of elements and measurements from the second set of elements, and to display on the display an image of the at least one portion of the object showing the effective atomic number of the portion.

13. A system according to claim 1, wherein the segmented array of detector elements includes a collimator to reduce fan beam penetrating radiation scattered from the segmented array of detectors and incident on the scatter detector.

14. A system for inspecting an object, the system comprising:
  a. a first radiation source that emits a fan beam of penetrating radiation;
  b. a segmented array of detector elements for measuring the intensity of penetrating radiation transmitted through the object from the first radiation source, the array including a collimator to intercept radiation scattered by the array;
  c. a second radiation source that emits a scanning pencil beam of penetrating radiation;
  d. at least one scatter detector for detecting penetrating radiation scattered out of the scanning pencil beam by the object, the scatter detector further including means for intercepting radiation scattered from the fan beam; and
  e. a processor, a memory and a display, the memory containing instructions that cause the processor:
    to subtract a background signal from a measured signal from the scatter detector, the background signal measured by the scatter detector when the second radiation source is not illuminating the object, thereby forming a corrected measured scatter signal, and
    to display on the display the corrected measured scatter signal and a measured transmission signal from the segmented array of detector elements for use in inspecting the object.

15. A system according to claim 14, wherein the first radiation source emitting the fan beam and the second radiation source emitting the scanning pencil beam are the same radiation source.

16. A system according to claim 14, wherein the segmented array of detector elements includes a first set of elements that measure radiation in a first energy range and a second set of elements that measure radiation in a second energy range and wherein the memory further includes instructions that cause the processor:
  to adjust the aspect ratio and size of the measured transmission signal and the corrected measured scatter signal such that the size and shape of the object appear similar in a display of the measured transmission signal and in a display of the corrected measured scatter signal,
  to determine the effective atomic number of at least one portion of the object using measurements from the first set of elements and measurements from the second set of elements, and
  to display on the display an image of the at least one portion of the object showing the effective atomic number of the portion.

* * * * *